United States Patent [19]

Brown et al.

[11] Patent Number: 5,312,983
[45] Date of Patent: May 17, 1994

[54] ORGANOMETALLIC TELLURIUM COMPOUNDS USEFUL IN CHEMICAL VAPOR DEPOSITION PROCESSES

[75] Inventors: Duncan W. Brown, Wilton, Conn.; Rein U. Kirss, Needham, Mass.; Douglas Gordon, Cornwall Bridge, Conn.

[73] Assignee: Advanced Technology Materials, Inc., Danbury, Conn.

[21] Appl. No.: 656,564

[22] Filed: Feb. 15, 1991

[51] Int. Cl.$^5$ .............................................. C07F 11/00
[52] U.S. Cl. ........................................................ 562/899
[58] Field of Search ........................................ 562/899

[56] References Cited

U.S. PATENT DOCUMENTS

| | | | |
|---|---|---|---|
| 4,256,912 | 3/1981 | Wolsky et al. | 562/899 X |
| 4,258,208 | 3/1981 | Kao et al. | 562/899 X |
| 4,508,662 | 4/1985 | Schack et al. | 562/899 |
| 4,578,225 | 3/1986 | Schack et al. | 562/899 |
| 4,675,088 | 6/1987 | Schack et al. | 562/899 X |
| 4,828,938 | 5/1989 | Lichtmann et al. | 428/689 |
| 4,920,068 | 4/1990 | Valentine et al. | 437/81 |

OTHER PUBLICATIONS

Kauermann et al., "C.A.", 109(7):54238g, 1988.
Herberg et al., "C.A.", 108(5):37998f, 1988.
Faye et al., "C.A.", 103(19):160622c, 1985.
Denniston et al., "C.A.", 83(19):163571q, 1975.
"An examination of organometallic thermal stability and its relevance to low temperature MOCVD growth of HgCdTe", W. E. Hoke; P. J. Lemonias; R. Korenstein, J. Mater. Res. 3, 329–334 (1988).
"Metalorganic growth of CdTe and HgCdTe epitaxial films at a reduced substrate temperature using diisopropyltelluride", W. E. Hoke; P. J. Lemonias, Appl. Phys. Lett. 46, 398–400 (1985).
"Low-temperature organometallic vapor phase epitaxial growth of CdTe using a new organotellurium source," D. W. Kisker; M. L. Skigerwald; T. Y. Kometani; K. S. Jeffers Appl. Phys Lett. 50, 1681.
"Temperature–independent unassisted pyrolytic MOCVD growth of cadmium telluride at 290° C. and mercury telluride at 325° C. using dimethylcadmium, methylallyltelluride, and dimethylmercury," J. D. Parsons; L. S. Lichtmann; J. Crystal Growth 86, 222–7 (1988).
"Temperature–independent unassisted pyrolytic MOCVD growth of cadmium telluride at 250° C. using 2,5-dihydrotellurophene," L. S. Lichtmann; J. D. Parsons; E.-H. Cirlin; J. Crystal Growth 86, 217–21 (1988).
CRC Handbook of Chemistry and Physics, 57th Edition, pp. C-495, C-505, C-712 (1976).
"Perfluoroalkyl tellunium compounds: Investigations on the preparation of bis(trifluoromethyl)tellurium," V. S. Herberg; D. Naumann; Z. Anorg. Allg. Chem. 492, 95–102 (1982).
"Bis(trifluoromethyl)mercury" R. Eujen; Inorg. Synth 24, 52–54 (1986).
"Synthesis and mechanistic studies of symmetric tetraorganyl tellurium (IV) ($R_4$Te) and Diorganyltellurium (II) ($R_2'$Te) compounds (R=R'=Me, n-Bu, Me$_3$SiCH$_2$, and CH$_2$=CH; R'=t-Bu and allyl)," R. W. Gedridge et al. Organometallics 10, 286–291 (1991).
"Tellurium Compounds," Computerized literature retrieval in Chemical Abstracts Registry File, Feb. 14, 1991.

Primary Examiner—Paul F. Shaver
Attorney, Agent, or Firm—Janet Elliott

[57] ABSTRACT

Novel tellurium compounds of the present invention have the formula:

$$TeR^1R^2$$

wherein $R^1$ is a fluorinated alkyl having the formula $C_nF_{(2n+1)-x}H_x$ where n may range from 1 to 6 and x may range from 0 to 2n, and $R^2$ is selected from the group consisting of alkyls having 2 to 6 carbon atoms, cycloalkyls having 3 to 6 carbon atoms, allyl, alkyl-substituted allyl having 4 to 6 carbon atoms, cyclopentadienyl, benzyl, alpha-methylbenzyl, and bis(alpha-methyl)benzyl. The novel tellurium reagents are useful as sources for organometallic vapor deposition processes, particularly the MOCVD fabrication of II–VI semiconductor materials such as $Hg_xCd_{1-x}Te$. The compounds are synthesized by high yield ligand exchange reactions between $Te(R^1)_2$ and $Te(R^2)_2$.

4 Claims, 1 Drawing Sheet

- □ (CF3Te-t-Bu), curve A
- ■ (CF3TeBz), curve B
- ♦ (MeTe-t-Bu), curve C

ORGANOMETALLIC TELLURIUM COMPOUNDS USEFUL IN CHEMICAL VAPOR DEPOSITION PROCESSES

FIELD OF THE INVENTION

The present invention relates to organometallic tellurium compounds useful as source reagents or precursors for source reagents in chemical vapor deposition (CVD) processes such as those employed in the fabrication of semiconductors.

BACKGROUND OF THE INVENTION

Semiconductor materials of the Group II-VI elements and especially those containing mercury, cadmium, and tellurium are useful as photodetectors for infrared radiation. Applications include heat sensors in automobile engines, solar cells, sensors for road obstacles, and infrared detectors for night vision and heat-seeking missiles.

In order to take advantage of the electronic properties for the II-VI materials, devices based on heterojunction diodes and superlattices must be fabricated. Device fabrication requires the ability to grow abrupt junctions over large areas but this has been hampered by the high temperatures required to grow tellurium containing alloys. The high growth temperatures coupled with low growth rates result in diffusion of mercury across the heterojunction, thus destroying its integrity and usefulness.

The apparent solution is to lower the growth temperatures and increase the growth rates. Metalorganic chemical vapor deposition (MOCVD) is a technique well-suited to the deposition of II-VI semiconductors. MOCVD is commonly employed in the semiconductor, optical, and optoelectronic industries for doping or coating a suitable substrate. MOCVD essentially involves depositing a thin film of an element or compound onto a substrate such as silicon. The deposited films can be sources of doping impurities which are driven into the substrate or the films themselves can have different electrical or optical properties than the substrate. The properties of the film depend on the deposition conditions and the chemical identity of the deposited film. MOCVD has significant advantages in that the process is uniform and amenable to scale-up. New source reagents and growth techniques that permit junction fabrication at low temperatures are required.

MOCVD of tellurium containing alloys is limited by the availability of appropriate tellurium source reagents. The most important criteria for effective reagents in low temperature CVD of tellurium are:

1) volatility of the tellurium source reagent,
2) efficient decomposition of the source reagent to elemental tellurium without incorporation of impurities into the product film, and
3) chemical and elemental purity of the source reagent.

The ideal reagent for CVD of a metal or metalloid element would be characterized by high volatility (vapor pressure of $\geq 10$ mm Hg at room temperature) and rapid low temperature decomposition to the elemental form (e.g., decomposition at temperatures of about 200° C. versus temperatures approaching 500° C., which are required for the presently available tellurium source reagents) with no codeposition of carbon or other contaminants into the film of the desired element. Dimethyl and diethyltellurium are currently utilized as source reagents for the CVD of tellurium and are commercially available. Neither of these reagents possesses labile Te-C bonds and both require high temperatures (>450° C.) for successful deposition of tellurium containing alloys (Hoke, W. E.; Lemonias, P. J.; Korenstein, R., J. Mater. Res., 1988, 3, 329).

No currently available tellurium source reagents are optimum for the intended applications. New tellurium reagents with weaker tellurium-carbon bonds have been introduced since 1985 and are included in the table below. The newer reagents have secondary or tertiary alkyl or allyl substituents, since it has been reasoned that these substituents will lead to enhanced decomposition at lower temperatures. While improvement is seen in the decomposition temperature, volatility of the starting reagent is sacrificed.

| Organotellurium Source Reagents | | |
|---|---|---|
|  | Growth Temp. (°C.) | Vapor Pressure (mm/°C.) |
| Dimethyltellurium | 450 | 51/25 |
| Diethytellurium | 450 | 9.3/25 |
| Diisopropyltellurium | 390 | 5.6/30 |
| Ditertbutyltellurium | 320 | 4/40 |
| Diallyltellurium | (280) | 3.5/45 |
| Methyl(allyl)tellurium | 290 | 8/30 |
| 2,5-dihydrotellurophene | 250 | — |
| Dimethylditellurium | (250) | 0.26/23 |

Hoke, W. E.; Lemonias, P., Appl. Phys. Lett., 1985, 46, 398. Kisker, D. W.; Steigerwald, M. L.; Kometani, T. Y.; Jeffers, K. S., Appl. Phys. Lett., 1987, 50, 1681. Parsons, J. D.; Lichtmann, L. S.; J. Cryst. Growth, 1988, 86, 222. Parsons, J. D.; Lichtmann, L. S.; J. Cryst. Growth, 1988, 86, 217.

Perfluoroalkyltellurium compounds represent a novel alternative to the materials currently in use, yet until now these reagents have not been studied under MOCVD conditions, nor in many cases even synthesized. The increased volatility for alkyl(perfluoroalkyl)-tellurium compounds, without significant alteration of growth temperatures or film quality, renders these compounds potentially superior source reagents for MOCVD.

The absence of intermolecular forces in perfluoroalkyl compounds often leads to increased volatility. Boiling points for a number of main group alkyl compounds are compared with the corresponding perfluoro alkyl compounds below and demonstrate the trend toward lower boiling points for the fluorocarbon derivatives.

| Boiling Points of Selected Organometallic Compounds at 1 atm | | | | | | |
|---|---|---|---|---|---|---|
| Compound | $(CH_3)_2S$ | $(CF_3)_2S$ | $(CH_3)_2Se$ | $(CF_3)_2Se$ | $(CH_3)_2Te$ | $(CF_3)_2Te$ |
| b.p. (°C.) | 37.3 | −22 | 54.5 | — | 82 | 23 |

CRC Handbook of Chemistry and Physics 55th Ed. 1974–75; Herberg, S.; Naumann, D., Z. Anorg. Allg. Chem., 1982, 492, 95

A further concern that arises in MOCVD of tellurium-containing materials is the high toxicity of hydrogen telluride or the dialkyltellurium compounds. In addition, these materials possess odors that are so foul and persistent that they are exceedingly unpleasant and inconvenient to work with. The excursion of even extremely small amounts of the lower alkyl tellurides into the air creates an intolerable working environment. Thus new organometallic compounds of tellurium, with enhanced volatility and reduced toxicity and stench factors, would be desirable.

SUMMARY OF THE INVENTION

It is therefore an object of the present invention to provide novel tellurium compounds that are useful as sources for organometallic vapor deposition processes, particularly the MOCVD fabrication of II-VI semiconductor materials such as $Hg_xCd_{1-x}Te$.

It is further an object of the present invention to provide new tellurium reagents that have higher volatility relative to previously used tellurium alkyls and that overcome the problems of high growth temperatures of the II-VI materials, high toxicity, and excessive stench.

It is still further an object of the present invention to provide tellurium source reagents that utilize fluorinated alkyl ligands, thereby to enhance volatility and reduce odor.

These and other objects are provided in the present invention which comprises novel tellurium compounds having the general formula:

$$TeR^1R^2$$

wherein $R^1$ is a fluorinated alkyl having the formula $C_nF_{(2n+1)-x}H_x$ where n may range from 1 to 6 and x may range from 0 to 2n, and $R^2$ is selected from the group consisting of alkyls having 2 to 6 carbon atoms, cycloalkyls having 3 to 6 carbon atoms, allyl, alkyl-substituted allyl having 4 to 6 carbon atoms, cyclopentadienyl, benzyl, alpha-methylbenzyl, and bis(alpha-methyl)benzyl.

In particular, the tellurium compounds in accordance with the present invention which are especially suitable for use in MOCVD processes are those that possess a fluorinated alkyl ligand such as trifluoromethyl and a secondary or tertiary alkyl or allyl ligand as the second substituent. Such compounds have the enhanced volatility provided by the fluorinated alkyl group and the ease of decomposition provided by the secondary or tertiary alkyl or allyl group.

DETAILED DESCRIPTION OF THE INVENTION

Figure 1:
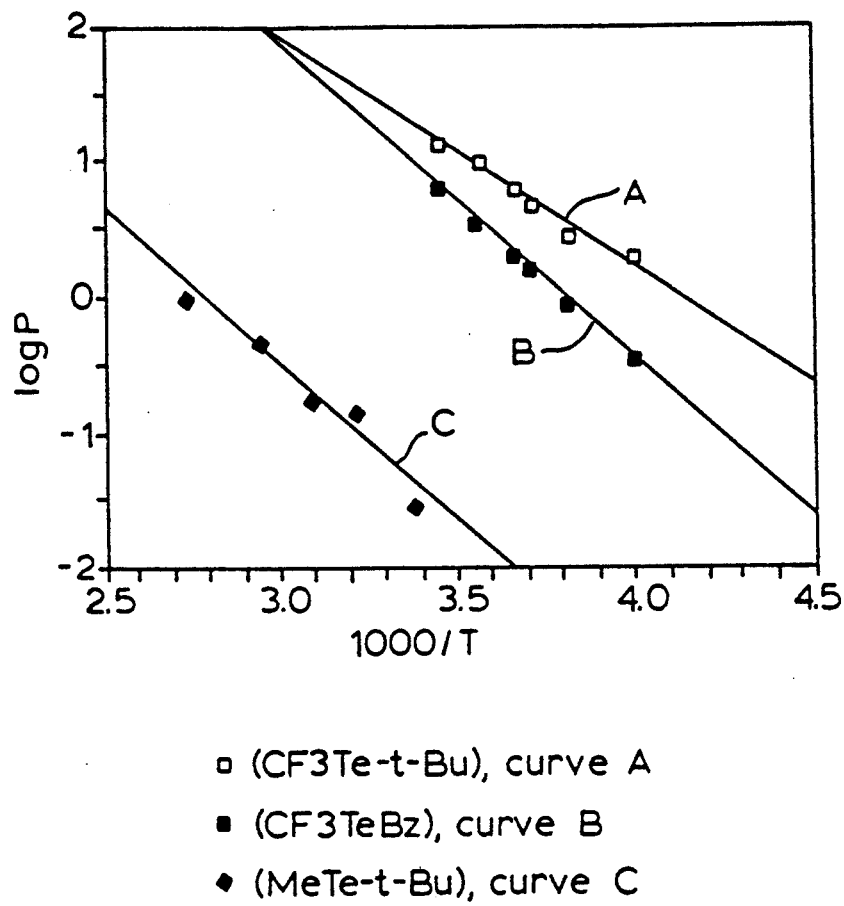
FIG. 1 shows a plot of log (vapour pressure) versus 1/T, where T is the temperature in degrees Kelvin, for two illustrative compounds of the present invention, trifluoromethyl(t-butyl)tellurium (curve A) and trifluoromethyl(benzyl)tellurium (curve B), and for a previously known non-fluorinated compound, methyl(t-butyl)tellurium (curve C), which is included for comparison.

The novel tellurium compounds of the present invention have the formula:

$$TeR^1R^2$$

wherein $R^1$ is a fluorinated alkyl having the formula $C_nF_{(2n+1)-x}H_x$ where n may range from 1 to 6 and x may range from 0 to 2n, and $R^2$ is selected from the group consisting of alkyls having 2 to 6 carbon atoms, cycloalkyls having 3 to 6 carbon atoms, allyl, alkyl-substituted allyl having 4 to 6 carbon atoms, cyclopentadienyl, benzyl, alpha-methylbenzyl, and bis(alpha-methyl)benzyl. The presence of the fluorinated alkyl groups enhances the volatility of the compounds. The presence of certain small alkyl groups promotes certain types of decomposition mechanisms. The presence of small groups can accelerate decomposition that proceeds through a disproportionation mechanism. The presence of beta hydrogen atoms can lead to decomposition via a beta-hydrogen elimination pathway. The behavior of the compounds depends strongly on the characteristics imparted by the substituent groups. The compounds that are most suitable for MOCVD are those that possess a small perfluorinated alkyl substituent and a secondary or tertiary alkyl or allyl group.

It is particularly preferred to employ trifluoromethyl(alkyl)tellurium or trifluoroethyl(alkyl)tellurium, where the alkyl group contains 6 or fewer carbons, trifluoromethyl(benzyl)tellurium or trifluoroethyl(benzyl)tellurium, or trifluoromethyl(allyl)tellurium or trifluoroethyl(allyl)tellurium in the MOCVD process. Trifluoromethyl(t-butyl)tellurium, trifluoromethyl(benzyl)tellurium, and trifluoromethyl(allyl)tellurium are particularly preferred because they have both the enhanced volatility provided by the trifluoromethyl substituent and the ready decomposition via beta hydrogen elimination provided by the t-butyl group or facile tellurium-carbon bond homolysis provided by the t-butyl, allyl, or benzyl substituents.

It is contemplated that a number of conventional methods known in the art could be used to synthesize the novel tellurium compounds of the present invention. However, in general the di-substituted tellurium compounds of the present invention are preferably prepared by allowing tellurium tetrachloride to react with bis(perfluoroalkyl)mercury ($R^1{}_2Hg$), to provide the bis(perfluoroalkyl)tellurium compound, which is then allowed to react with a stoichiometric amount of dialkyltellurium ($TeR^2$), thereby to undergo a ligand exchange reaction to produce the novel tellurium compounds of the present invention, $TeR^1R^2$. Preparation of these compounds, exemplified by the trifluoromethyl(alkyl)telluriums, is readily accomplished as follows:

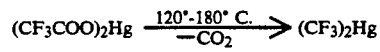

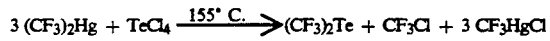

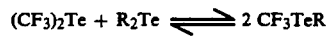

The trifluoromethyl(alkyl)telluriums prepared by this synthetic approach showed significant increases in volatility as compared to the alkyltellurium compounds. The vapor pressure of trifluoromethyl(t-butyl)tellurium compound is compared with values for methyl(t-butyl)tellurium and bis(t-butyl)tellurium below:

| Vapor Pressures of Selected t-Butyltelluriums | |
|---|---|
| Compound | Vapor Pressure (mm Hg/°C.) |
| $CF_3TeC(CH_3)_3$ | 13/17 |
| $CH_3TeC(CH_3)_3$ | 0.8/17 |
| $(CH_3)_3CTeC(CH_3)_3$ | 4/40 |

FIG. 1 shows plot of the logarithm of vapor pressure in mm Hg versus 1/T, where T is the temperature is degrees Kelvin, for two illustrative compounds of the present invention, trifluoromethyl(t-butyl)tellurium (curve A) and trifluoromethyl(benzyl)tellurium (curve B). The previously known non-fluorinated compound, methyl(t-butyl)tellurium (curve C), is included for comparison. This plot shows that in the temperature range of interest, 273 K to 298 K, the novel fluorinated tellurium source reagents of the present invention possess useful vapor pressures. Indeed, the vapor pressures of the novel fluorinated compounds A and B are surprisingly and unexpectedly higher than the fully hydrogen-substituted analogs.

An especially useful attribute of the trifluoromethyl(alkyl)tellurium compounds that were prepared as described above is their apparently total lack of offensive odor. This advantage is somewhat surprising, since these compounds do contain an alkyl group similar to the dimethyltellurium, diethyltellurium, or bis(t-butyl)tellurium compounds, which are extremely foul smelling.

Trifluoromethyl(t-butyl)tellurium decomposes under MOCVD conditions at temperatures (275°–325°) identical to the decomposition temperature range of bis(t-butyl)tellurium and comparable to the best tellurium source reagents currently available or under development for MOCVD of tellurium alloys, yet is has a 15-fold greater vapor pressure at room temperature. The products (isobutene, isobutane and bis(trifluoromethyl)tellurium) are stable under the growth conditions and are thus unlikely to contribute contaminants to the growing film. These products indicate a decomposition mechanism similar to that observed for bis(t-butyl)tellurium and show that the decomposition mechanism is influenced primarily by the alkyl substituent without being adversely affected by the trifluoroalkyl substituent, which gives the novel compounds their enhanced volatility.

The synthetic scheme for trifluoromethyl(alkyl)telluriums, such as trifluoromethyl(t-butyl)tellurium, described above, is extremely well suited to scaleup. The decarboxylation of mercuric trifluoroacetate can be carried out on a large scale to produce bis(trifluoromethyl)mercury with a yield of 55% (Eujen, R., *Inorg. Synth.*, 1986, 24, 52). The reaction of bis(trifluoromethyl)mercury with tellurium (IV) chloride in a stainless steel reactor proceeds with yields of 65–75%. Reactors of this type are available in very large sizes and are capable of withstanding the high pressures of $CF_3Cl$ produced. The synthesis of bis(t-butyl)tellurium is straightforward and proceeds in high yield (Gedridge, R. L., et al. *Organometallics*, 1991, 10, 286). Finally, the ligand exchange reaction can easily be run on a large scale and produces excellent yields of the desired compound. It is important to note that, with the exception of the bis(t-butyl)tellurium synthesis, all of these reactions are carried out between solids or neat liquids, thus minimizing potential contamination from oxygenated solvents. Purification by careful distillation of the intermediate bis(t-butyl)tellurium and the final product produces high purity material for MOCVD. The primary impurities which have been observed ($CF_2Cl_2$, $CF_3Cl$, t-$Bu_2Te$) have widely different boiling points than the desired product and are readily separated by distillation.

The novel tellurium compounds of the present invention can thus be usefully employed in a number of chemical vapor deposition processes, particularly those involving the fabrication of II-VI semiconductor materials. The unique characteristics of these compounds, particularly their high volatility and lack of offensive odor, make these compounds particularly well-suited for use in organometallic chemical vapor deposition processes.

The following examples are provided to further exemplify the production of compounds of the present invention. These examples are presented for illustrative purposes only, and are not in any way intended to limit the scope of the present invention. It is possible that alternative synthesis methods may be used by those of ordinary skill in the art to manufacture the compounds of the present invention.

EXAMPLES

EXAMPLE 1

Synthesis of trifluoromethyl(benzyl)tellurium

Dibenzyltellurium (2.44 g, 0.00788 moles) was placed in a 50 ml flask equipped with a vacuum stopcock and magnetic stirrer. Bis(trifluoromethyl)tellurium (1.93 g, 0.00727 moles) was condensed into the flask and the mixture was stirred at room temperature, exposed to artificial room light, for 65 hours. The flask was fitted with a short path distillation head and trifluoromethyl(benzyl)tellurium (3.0 g, 72% yield) was distilled from the reaction mixture under vacuum (b.p. 15°–23°/0.1 torr) and isolated in >99.9% purity. The nuclear magnetic resonance (NMR) spectrum of the trifluoromethyl(benzyl)tellurium product dissolved in deuterated benzene ($C_6D_6$) showed the following peaks: $^1H$: $\delta$6.95 (m, 5H), 3.94 (s, 2H) ppm; $^{125}Te$: 976 ppm (q of t, $J_{Te-F}$=92 Hz, $J_{Te-H}$=24 Hz). Mass spectroscopic analysis revealed peaks at m/z 290 ($M^+$), 199 ($CF_3Te^+$), 130 ($Te^+$), 91 ($C_6H_5CH_2^+$). The only identifiable impurity by gas chromatography/mass spectrometry (GC/MS) was bis(trifluoromethyl)tellurium.

EXAMPLE 2

Synthesis of trifluoromethyl(t-butyl)tellurium

Using the method of Example 1, bis(t-butyl)tellurium (0.51 g, 0.0021 moles) was allowed to react with $(CF_3)_2Te$ (0.50 g, 0.0019 moles) for 24 hours at room temperature, exposed to light. Fractionation of the volatile products on a vacuum line gave trifluoromethyl(t-butyl)tellurium (0.89 g, 92% yield) contaminated with ~2% bis(t-butyl)tellurium. NMR($C_6D_6$) $^1H$: $\delta$1.42 (s, 9H) ppm; $^{125}Te$: 1155 ppm (q, $J_{Te-F}$=55 Hz). Mass spec: m/z 256 ($M^+$), 199 ($CF_3Te^+$), 130 ($Te^+$), 69 ($CF_3^+$), 57 ($C_4H_9^+$).

EXAMPLE 3

Synthesis of trifluoromethyl(allyl)tellurium

Equimolar amounts of diallyltellurium and bis(trifluoromethyl)tellurium were combined under vacuum in a flame-sealed NMR tube. After 14 days at room temperature, exposed to light, a new resonance in the $^{125}Te$ NMR was seen at 893 ppm (q of t, $J_{Te-F}$=92 Hz, $J_{Te-H}$=30 Hz). GC/MS of the mixture confirmed the presence of trifluoromethyl(allyl)tellurium: m/z 240 ($M^+$), 199 ($CF_3Te^+$), 171 ($C_3H_5Te^+$), 130 ($Te^+$), 69 ($CF_3^+$), 41 ($C_3H_5^+$).

The organometallic tellurium compounds and synthesis process of the present invention offer many functionally significant advantages. Proper selection of the alkyl and fluoroalkyl substituents allows control of the vapor pressure and decomposition temperature. The compounds may be used without the severe stench disadvantage of previous tellurium CVD source reagents. Various modifications are possible within the spirit and scope of the present invention.

What is claimed is:

1. A compound having the formula:

TeR$^1$R$^2$ wherein R$^1$ is a fluorinated alkyl having the formula C$_n$F$_{(2n+1)-x}$H$_x$; and where n ranges from 1 to 6 and x ranges from 0 to 2 n; and R$^2$ is selected from the group consisting of secondary and tertiary alkyls having 3 to 6 carbon atoms, cycloalkyls having 3 to 6 carbon atoms, allyl, alkyl-substituted allyls having 4 to 6 carbon atoms, cyclopentadienyl, benzyl, alpha-methylbenzyl, and bis-(alpha-methyl)benzyl.

2. A compound according to claim 1 wherein R$^1$ is selected from the group consisting of trifluoromethyl and pentafluoroethyl.

3. A compound having the formula:

TeR$^1$R$^2$ wherein R$^1$ is selected from the group consisting of trifluoromethyl and pentafluoroethyl and R$^2$ is selected from the group consisting of t-butyl, i-propyl, allyl, and benzyl.

4. A compound having the formula

TeR$^1$R$^2$ wherein R$^1$ is trifluoromethyl and R$^2$ is selected from the group consisting of t-butyl and allyl.

* * * * *